United States Patent
Yamada et al.

(10) Patent No.: US 11,965,099 B2
(45) Date of Patent: Apr. 23, 2024

(54) DIOXAZINE PIGMENT AND COLORANT

(71) Applicant: DIC CORPORATION, Tokyo (JP)

(72) Inventors: Shogo Yamada, Kamisu (JP);
Hiromasa Kikuchi, Kamisu (JP);
Hidehiro Otake, Kamisu (JP)

(73) Assignee: DIC CORPORATION, Tokyo (JP)

( * ) Notice: Subject to any disclaimer, the term of this patent is extended or adjusted under 35 U.S.C. 154(b) by 0 days.

(21) Appl. No.: 17/979,240

(22) Filed: Nov. 2, 2022

(65) Prior Publication Data
US 2023/0067213 A1 Mar. 2, 2023

Related U.S. Application Data

(62) Division of application No. 16/757,541, filed as application No. PCT/JP2018/042259 on Nov. 15, 2018, now abandoned.

(30) Foreign Application Priority Data

Nov. 28, 2017 (JP) .................. 2017-227804

(51) Int. Cl.
*C09B 19/00* (2006.01)
*C07D 498/22* (2006.01)
*C09D 11/037* (2014.01)

(52) U.S. Cl.
CPC ............ *C09B 19/00* (2013.01); *C07D 498/22* (2013.01); *C09D 11/037* (2013.01)

(58) Field of Classification Search
CPC ...... C09B 19/00; C07D 498/22; C09D 11/037

USPC ....................................................... 106/31.77
See application file for complete search history.

(56) References Cited

U.S. PATENT DOCUMENTS

2010/0128375 A1 5/2010 Kudou et al.
2012/0018687 A1 1/2012 Jung et al.

FOREIGN PATENT DOCUMENTS

| JP | H09286947 A | 11/1997 |
| JP | 2011-162662 A | 8/2011 |

OTHER PUBLICATIONS

International Search Report dated Dec. 18, 2018, issued in counterpart International Application No. PCT/JP2018/042259 (2 pages).
Supplementary European Search Report dated Sep. 10, 2021, issued in EP Application No. 18 88 3946.8. (2 pages).
Non-Final Office Action dated Jul. 25, 2022, issued in U.S. Appl. No. 16757,541.

*Primary Examiner* — Kahsay Habte
(74) *Attorney, Agent, or Firm* — WHDA, LLP

(57) ABSTRACT

An object of the present invention is to provide a dioxazine pigment having excellent fluidity. More specifically, an object of the present invention is to provide a dioxazine pigment in which practically sufficient fluidity is attained in both (1) initial viscosity and (2) storage stability when the dioxazine pigment is used in a printing ink application. The object is attained by providing a dioxazine pigment having a contact angle with respect to water according to an infiltration rate method in a range of 30° to 75°, and a contact angle with respect to 1-bromonaphthalene according to an infiltration rate method in a range of 30° to 75°.

2 Claims, No Drawings

DIOXAZINE PIGMENT AND COLORANT

CROSS-REFERENCE TO RELATED APPLICATIONS

This application is a divisional of U.S. application Ser. No. 16/757,541, filed on Apr. 20, 2020, which is a 371 of International Application No. PCT/JP2018/042259, filed on Nov. 15, 2018, which is based upon and claims the benefit of priority from Japanese Patent Application No. 2017-227804, filed on Nov. 28, 2017, the entire contents of which are incorporated herein by reference.

TECHNICAL FIELD

The present invention relates to a dioxazine pigment that can be used in an extensive application such as a printing ink, a coating material, a colored molded article, and textile printing.

BACKGROUND ART

In general, a pigment for coloring contains fine particles. For example, in a case where a pigment that is an aggregate of fine primary particles, such as a printing ink of gravure printing, flexo printing, or the like, or a coating material, is dispersed in a medium, in order to loosen the aggregation of the particles, devisal such as performing dispersion for a long period of time by applying a strong force or adding a dispersant has been conducted.

Among them, a dioxazine pigment represented by C.I. Pigment Violet 23 is a pigment that is used in various situations, but easily causes stacking structurally and tends to be rigidly aggregated, and thus, problems relevant to fluidity are considerable when the dioxazine pigment is used in various applications as a colorant. Therefore, in order to improve the fluidity, the combination of a derivative of the dioxazine pigment has been considered (PTL 1 or the like).

However, in a method of combining a pigment derivative, there is a case where it is not possible to sufficiently ensure the fluidity, depending on an application.

For this reason, there is still a demand for improving a dioxazine pigment exhibiting sufficient fluidity.

CITATION LIST

Patent Literature

PTL 1: JP-A-2011-162662

SUMMARY OF INVENTION

Technical Problem

In consideration of the circumstances as described above, an object of the present invention is to provide a dioxazine pigment having excellent fluidity. More specifically, an object of the present invention is to provide a dioxazine pigment in which practically sufficient fluidity is attained in both (1) an initial viscosity and (2) storage stability when the dioxazine pigment is used in a printing ink application.

Solution to Problem

The present inventors have intensively studied a mutual interaction in a plurality of components in a printing ink in order to find a dioxazine pigment exhibiting more excellent fluidity, and as a result thereof, have found that the object can be attained by preparing a dioxazine pigment to have specific contact angles with respect to water and an organic solvent, respectively, by modifying the surface of the pigment particles, and have completed the present invention.

That is, the present invention relates to:

"Claim 1. A dioxazine pigment having a contact angle with respect to water according to an infiltration rate method in a range of 30° to 75°, and a contact angle with respect to 1-bromonaphthalene according to an infiltration rate method in a range of 30° to 75° (hereinafter, may be referred to as the dioxazine pigment of the present invention).

Claim 2. The dioxazine pigment according to claim 1, wherein dioxazine pigment particles have at least one hydroxy group and at least one carbonyl group on a surface thereof.

Claim 3. A colorant containing at least the dioxazine pigment according to claim 1 or 2."

Advantageous Effects of Invention

According to the dioxazine pigment of the present invention, a remarkable effect is obtained in which a dioxazine pigment having excellent fluidity at the time of being used in a printing ink or the like can be obtained. More specifically, when the dioxazine pigment is used in a printing ink application, practically sufficient performance is exhibited in both (1) an initial viscosity and (2) storage stability. In addition, the gloss of a printed material is also excellent. Further, the dioxazine pigment of the present invention is not based on a derivative treatment, and thus, it is possible to eliminate the possibility that undesirable influence such as migration due to the derivative treatment described above occurs.

DESCRIPTION OF EMBODIMENTS

Hereinafter, the present invention will be described in detail.

The present invention relates to a dioxazine pigment having a contact angle with respect to water according to an infiltration rate method in a range of 30° to 75°, and a contact angle with respect to 1-bromonaphthalene according to an infiltration rate method in a range of 30° to 75°. According to such a dioxazine pigment of the present invention, excellent fluidity is exhibited even when the dioxazine pigment is used as a printing ink or a coating material.

<Description of Dioxazine Pigment>

Examples of the dioxazine pigment used in the present invention include C.I. Pigment Violet 23, C.I. Pigment Violet 37, C.I. Pigment Blue 80, and the like. In particular, C.I. Pigment Violet 23 is industrially important, and is represented by Chemical Structural Formula (I) described below. As such C.I. Pigment Violet 23, a commercially available product (for example, FASTOGEN SUPER VIOLET series (manufactured by DIC Corporation, Specific Surface Area according to BET Method: 50 $m^2$/g to 120 $m^2$/g), and the like) may be used, or a pigment produced by a known conventional method may be used. The produced pigment may be subjected to a known treatment suitably. It is preferable that the specific surface area of the C.I. Pigment Violet 23 according to the BET method is in a range of 60 $m^2$/g to 80 $m^2$/g, from the viewpoint of preventing thickening due to excessive aggregation of fine particles while retaining transparency.

[Chem. 1]

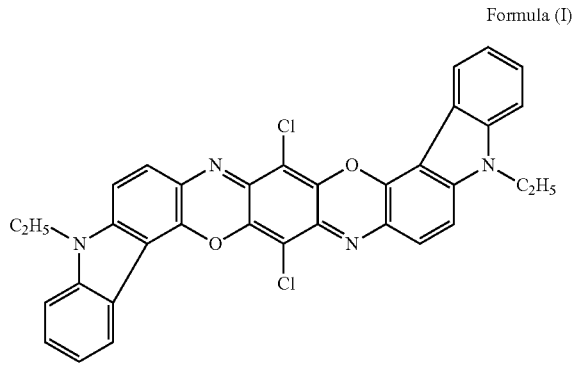 [SMILES: CCn1c2ccccc2c2c3c(ccc21)N=c1c(Cl)c2c(c(Cl)c1O3)=Nc1ccc3c(c1O2)c1ccccc1n3CC]

Formula (I)

<Description of Contact Angle According to Infiltration Rate Method>

The present inventors have found that by preparing the dioxazine pigment in which the contact angle with respect to water according to the infiltration rate method described below is in a range of 30° to 75°, and the contact angle with respect to 1-bromonaphthalene is in a range of 30° to 75°, excellent fluidity can be obtained in a nitrocellulose (hereinafter, referred to as NC)-based ink and a polyurethane (hereinafter, referred to as PU)-based ink, that is, remarkably excellent thickening suppression can be obtained in both an initial viscosity and storage stability.

In the idea of the configuration described above, the present inventors have paid attention to a step of dispersing a pigment at the time of preparing various printing inks.

In the detailed description, a dispersion step of the dioxazine pigment includes a procedure of wetting an aggregate of dioxazine pigment particles in a solvent, and then, a procedure of mechanically crushing the aggregate into pigment particles, and finally, a procedure of performing dispersion stabilization in which a resin or the like is adsorbed on the surface of the pigment particles in order to prevent re-aggregation. Accordingly, as the wetting of the pigment with respect to the solvent is performed faster, time required to proceed to the next crushing procedure is shortened, and thus, the dispersion progresses faster. For example, in the PU ink, in a case where the wetting with respect to the solvent is performed fast and it is easy to proceed to the dispersion stabilization, the initial viscosity of the PU ink decreases and the storage stability is also excellent. In addition, the pigment is sufficiently dispersed, and the aggregate of the pigment particles decreases, and thus, the gloss of a printed material increases.

Similarly, in the NC ink, the dispersion is performed fast, in accordance with the improvement of the wettability, and the storage stability is excellent. Here, in the case of describing the NC ink as an example, ethanol that excellently dissolves NC and has comparatively high safety with respect to a human body may be used as a solvent of the NC ink. In addition, a method is known in which the NC ink containing ethanol is diluted with ethyl acetate such that a boiling point of the solvent is decreased, and thus, the drying of the ink is performed faster, and printing is performed at a high rate. When the NC ink of the dioxazine pigment is diluted with ethyl acetate, in general, the dioxazine pigment has low wettability and low affinity with respect to ethyl acetate, and thus, surface free energy of the pigment particles increases, and the stabilization is not attained. Accordingly, it is considered that a force for reducing a surface area of the pigment particles acts in order to decrease the surface free energy, and the aggregation of the pigment particles occurs. For this reason, the present inventors have considered that in a case where the dioxazine pigment has suitable affinity with respect to ethyl acetate and ethanol, both of the storage stability of the NC ink containing ethanol as a main solvent and the fluidity of the NC ink after being diluted with ethyl acetate are retained. Therefore, a contact angle with respect to each medium has been examined by trial and error, and thus, it has been found that in the dioxazine pigment prepared such that the contact angle is in the range described above, "the affinity of the dioxazine pigment with respect to ethyl acetate and ethanol", which is the estimation mechanism described above, is suitable, and excellent fluidity can be maintained.

The contact angle was measured by the infiltration rate method, as follows. Herein, a numerical value of the contact angle is obtained by the following method. An automatic surface tensiometer Processor Tensiometer K12 (manufactured by KRUSS GmbH) was used. 1.5 g of a dioxazine pigment was filled in a measurement holder, a measurement liquid was infiltrated from the lower portion of the holder, and a wetting rate was measured as an option for measuring a powder wetting rate of the automatic surface tensiometer. First, a wetting rate of n-hexane was measured, an infiltration contact angle was assumed as 0°, and a filling constant was measured. Each dioxazine pigment was standardized on the basis of the measured filling constant such that a filling state thereof was the same. Subsequently, a wetting rate of each of water and 1-bromonaphthalene was measured, and the contact angle of the dioxazine pigment with respect to each of water and 1-bromonaphthalene was calculated by Washburn equation.

Examples of another method of measuring a contact angle of a powder such as a dioxazine pigment include a droplet method. The droplet method is a method in which a powder is subjected to tableting by using a tablet molding machine, a measurement solvent is dropped onto the surface of a sample in the shape of a flat plate, and a contact angle between the sample and the solvent is measured. However, the contact angle is affected by concavities and convexities of the sample in the shape of a tablet, and thus, in the measurement of the contact angle of the powder according to the droplet method, an error is comparatively large. In addition, the viscosity of most organic solvents is small, and thus, a liquid droplet of the organic solvent on the tablet is in a flat shape, and a contact angle is small, and therefore, a difference in the contact angles between the samples occurs. Such disadvantages of the droplet method can be solved by the measurement of the contact angle according to the infiltration rate method described above. Note that, from the relationship of the error, and the like, the contact angle according to the infiltration rate method, and the contact angle according to the droplet method are not necessarily coincident with each other.

Specifically, it is preferable that the dioxazine pigment exhibiting physical properties described above (the specific contact angle) does not have both a hydrophilic functional group and a hydrophobic functional group on the surface of the dioxazine pigment particles. The functional group is not particularly limited insofar as a contact angle with respect to water and 1-bromonaphthalene satisfies the specific range described above, and in a case where the dioxazine pigment has at least one hydroxy group and at least one carbonyl group on the surface of the dioxazine pigment, the dioxazine pigment exhibits particularly excellent fluidity at the time of being used in the preparation of an ink. It is estimated that the hydroxy group contributes to the improvement of wettability with respect to a hydrophilic solvent such as ethanol, and the carbonyl group contributes to the improvement of wettability with respect to a hydrophobic solvent such as ethyl acetate. In addition, the functional group contributes to the wetting of the pigment with respect to the solvent in the dispersion step, and then, mutually interacts with a binder resin such as NC or PU, in a dispersion stabilization step, and adsorbs the binder resin in the surface of the pigment particles, and thus, also contributes to the dispersion stabilization.

In general, the organic pigment is particles in which tens of thousands to millions of pigment molecules are bonded, and the same applies to the dioxazine pigment. In consideration of the wettability of the pigment with respect to the solvent, the site of the pigment particles relevant to the wettability is the outermost surface of the pigment particles which is directly in contact with the solvent. Accordingly, it is sufficient that the functional group exists on the surface of the pigment particles. The functional group is substituted with the pigment molecules on the outermost surface of the dioxazine pigment particles. It is difficult to specify a substitution position of the functional group in the pigment molecules, and it is estimated that the substitution is mainly performed on an aromatic ring. At this time, the hydrophilic functional group and the hydrophobic functional group may exist in one pigment molecules, or a pigment molecule having a hydrophilic functional group and a pigment molecule having a hydrophobic functional group may separately exist on the surface of the pigment particles.

Here, examples of the hydrophilic functional group include a hydroxy group or an amino group, a sulfo group, a thiol group, a carboxy group, or salts thereof, and the like.

In addition, examples of the hydrophobic functional group include a carbonyl group in which carbon atoms on the dioxazine pigment particles are bonded with an oxygen atom through a double bond, a functional group having other carbonyl groups, and specifically, a ketone group, an ester bond, an amide bond, a urethane bond, and the like.

<Production Method>

Here, an example of a method of preparing the dioxazine pigment in which the contact angle with respect to water according to the infiltration rate method is in a range of 30° to 75°, and the contact angle with respect to 1-bromonaphthalene according to the infiltration rate method is in a range of 30° to 75° will be described. However, the idea of the present invention is as described above, and any method may be adopted insofar as the dioxazine pigment can be prepared such that the contact angle is in the numerical range described above.

An example of a method of simply obtaining the dioxazine pigment of the present invention will be described below, but the present invention is not limited thereto. The dioxazine pigment of the present invention is obtained through a pigment slurry producing step of adding a dioxazine pigment that is a raw material into a solvent, of performing stirring, and of obtaining a pigment slurry, a pigment surface treatment step of adding an iron salt and hydrogen peroxide into the pigment slurry, of performing stirring, and of treating the surface of the pigment, and a step of filtering a reaction liquid, and of drying and pulverizing a filter product.

Examples of the dioxazine pigment that is the raw material include C.I. Pigment Violet 23, C.I. Pigment Violet 37, C.I. Pigment Blue 80, and the like. In particular, C.I. Pigment Violet 23 having high color strength and excellent weather resistance is industrially preferable. A commercially available dioxazine pigment or a dioxazine pigment that is produced by a known conventional method can be used as the dioxazine pigment that is the raw material, and for example, a method described in High Performance Pigments published by Wiley-VCH Verlag-GmbH (2002), Page 186 can be used as the known conventional method. The dioxazine pigment that is the raw material may be a dioxazine pigment without any treatment, or may be a dioxazine pigment in which the surface of pigment particles is treated with a pigment derivative such as a dioxazine pigment sulfonic acid derivative, an amino group-containing dioxazine pigment derivative, and a phthalimide methyl group-containing dioxazine pigment derivative, macromolecules such as a dispersant, a surfactant, rosin, or the like. In addition, other surface treatments of pigment particles may be performed with the pigment derivative such as the dioxazine pigment sulfonic acid derivative, the amino group-containing dioxazine pigment derivative, and the phthalimide methyl group-containing dioxazine pigment derivative, the macromolecules such as the dispersant, the surfactant, the rosin, and the like, after the pigment surface treatment step.

As the dioxazine pigment that is the raw material, a dioxazine pigment having a pigment particle diameter and a particle shape that are adjusted through a pigmentation step may be used, or a dioxazine pigment crude having a pigment particle diameter and a particle shape that are not adjusted may be used, and the pigment forming step may be performed after the pigment surface treatment step. For example, as the pigment forming step, one of an acid paste method, an acid slurry method, a dry milling method, a solvent method, a solvent milling method, and the like can be selected or a plurality thereof can be selected by being combined.

Water and/or an organic solvent can be used as the solvent, and methanol, ethanol, n-propanol, i-propanol, and the like can be used as the organic solvent. In particular, water is preferable from the viewpoint of economic efficiency. In addition, water may be pure water or may be industrial water, and a buffer solution such as an acetic acid buffer solution, a phosphoric acid buffer solution, a citric acid buffer solution, a citric acid-phosphoric acid buffer solution, a boric acid buffer solution, and a tartaric acid buffer solution may be used.

It is preferable that the added amount of the dioxazine pigment that is the raw material is 1 part by mass to 30 parts by mass with respect to 100 parts by mass of the solvent, and when the added amount is small, productivity is low, and when the added amount is large, the pigment slurry has a high viscosity, and excessive energy is required for stirring, and thus, the added amount of the dioxazine pigment is more preferably 2 parts by mass to 20 parts by mass, and is particularly preferably 3 parts by mass to 12 parts by mass, with respect to 100 parts by mass of the solvent.

Iron sulfate, iron chloride, iron fluoride, iron bromide, iron iodide, iron nitrate, iron phosphate, iron borate, iron carbonate, iron acetate, and the like can be used as the iron salt. Iron sulfate, iron chloride, and iron nitrate are preferable from the viewpoint of economic efficiency. Divalent iron can be used as iron. In addition, the iron salt may be an anhydride, or may be a hydrate.

It is preferable that a temperature in the pigment slurry producing step is 0° C. to 100° C. In addition, it is preferable that a temperature in the pigment surface treatment step is 0° C. to 100° C., and a reaction rate of a treatment reaction of the pigment surface is slow at a low temperature, and the decomposition of hydrogen peroxide is accelerated at a high temperature, and thus, the temperature in the pigment surface treatment step is more preferably 10° C. to 90° C., and is particularly preferably 20° C. to 80° C.

It is preferable that a reaction time in the pigment surface treatment step is 10 minutes to 2 hours.

It is preferable that the pH of a treatment liquid in the pigment surface treatment step is pH 1 to pH 7 since iron ions are precipitated by alkaline properties.

It is preferable that 1 mass % to 100 mass % of hydrogen peroxide is added with respect to the dioxazine pigment that is the raw material. When the added amount of the hydrogen peroxide is small, a surface treatment of the dioxazine pigment is insufficient, and the surface of the pigment particles is finite and excessive addition is economically disadvantageous, and thus, the added amount of the hydrogen peroxide is more preferably 3 mass % to 90 mass %, and is particularly preferably 6 mass % to 80 mass %.

It is preferable that 1 mass % to 30 mass % of the iron salt is added with respect to the dioxazine pigment that is the raw material. The iron salt functions as a catalyst of a surface treatment reaction of the pigment, and thus, when the added amount of the iron salt is small, a reaction rate of the surface treatment reaction is slow, and excessive addition accelerates the decomposition of hydrogen peroxide and is economically disadvantageous, and therefore, it is preferable that the added amount of the iron salt is 2 mass % to 15 mass %.

The iron salt and hydrogen peroxide may be simultaneously added or separately added to the pigment slurry. In a case where the iron salt and hydrogen peroxide are simultaneously added, hydrogen peroxide is decomposed when hydrogen peroxide and the iron salt are mixed in advance mix, and thus, hydrogen peroxide and the iron salt are mixed in the pigment slurry. In a case where the iron salt and hydrogen peroxide are separately added, the iron salt may be added first, or hydrogen peroxide may be added first. In addition, hydrogen peroxide may be added dropwise or may be added all at once.

According to the producing method described above, a hydroxy group and a carbonyl group are generated on the surface of the dioxazine pigment particles, and thus, it is possible to obtain a dioxazine pigment having at least one hydroxy group and at least one carbonyl group on the surface of the dioxazine pigment, which is another aspect of the present invention.

For example, in the producing method described above, it is possible to more preferably obtain the dioxazine pigment having at least one hydroxy group and at least one carbonyl group on the surface of the dioxazine pigment, by preparing treatment conditions of the surface of the dioxazine pigment particles, such as the type of solvent, the treatment temperature, and the amount of iron salt and hydrogen peroxide.

The dioxazine pigment having at least one hydroxy group and at least one carbonyl group on the surface of the dioxazine pigment, which is another aspect of the present invention, is preferable since the dioxazine pigment exhibits excellent fluidity, and has the following advantages.

In a fluidity improving method of the related art, the fluidity is not sufficiently improved depending on an application, as described above. In addition, depending on an application, there is a case where it is difficult to make the fluidity and demand characteristics other than the fluidity compatible due to the undesired influence of the derivative treatment for improving the fluidity. For example, in a dioxazine pigment that is used in a gravure ink for food packaging, the fluidity and retort resistance are required to be compatible with each other, but in a case where the fluidity is improved by the combination of the pigment derivative, the pigment derivative having dye properties is easily migrated to a base material (a film), and thus, the retort resistance tends to decrease.

As described above, according to the present invention in which the surface of the dioxazine pigment itself is modified, an undesired effect due to the derivative treatment for improving the fluidity, which has been a concern from the related art, can also be avoided.

<Mixed Color Stability>

The present inventors have further pursued the improvement of dispersion stability performance, and as a result thereof, have found that the dioxazine pigment of the present invention is also capable of solving the thickening at the time of being mixed with a blue ink containing copper phthalocyanine.

According to the consideration of the present inventors, such thickening at the time of mixing a violet ink with a blue ink occurs in the following case. That is, before color mixture, the binder resin in the ink is adsorbed in each of the dioxazine pigment and copper phthalocyanine, and thus, dispersion stabilization is obtained. On the other hand, it is considered that after the color mixture, binder resin adsorbed in the dioxazine pigment is adsorbed in copper phthalocyanine having stronger affinity with respect to the binder resin, and thus, the aggregation of the dioxazine pigment occurs, and the fluidity decreases. Here, in the violet ink containing the dioxazine pigment of the present invention, as described above, the binder resin is strongly adsorbed in the dioxazine pigment, and dispersion stability is high. Accordingly, it is estimated that even in a case where the violet ink is mixed with the blue ink, the dispersion of the dioxazine pigment and the copper phthalocyanine pigment is retained, and the fluidity is maintained.

Copper phthalocyanine is preferable as a color material of the blue ink, from the viewpoint of a color phase, toughness, economic efficiency, and the like. In addition, the copper phthalocyanine may be copper phthalocyanine without any treatment, or may be copper phthalocyanine in which the surface of pigment particles is treated with a pigment derivative such as a copper phthalocyanine sulfonic acid derivative, an amino group-containing copper phthalocyanine derivative, and a phthalimide methyl group-containing copper phthalocyanine derivative, macromolecules such as a dispersant, a surfactant, rosin, or the like. In addition, the violet ink containing the dioxazine pigment of the present invention and the blue ink can be mixed in a wide ratio in order to impart a reddish color to the blue ink or to reproduce deep purple blue.

Note that, the dioxazine pigment of the present invention can be adjusted to be suitable for each application by further containing an additive, a dispersant, or the like, unless undesired influence is exerted on the effects of the present invention.

The dioxazine pigment of the present invention obtained as described above can be preferably used in any application insofar as a coloring function is required. For example, the dioxazine pigment can be used in various known conventional applications such as a coating material, a printing ink, a colored molded article, a toner for developing an electrostatic charge image, a color filter of a liquid crystal display device, and a water-based ink for ink jet recording.

The dioxazine pigment of the present invention is capable of providing a printing ink that is excellent in the initial viscosity and is also excellent in the storage stability. The printing ink can be prepared by mixing various known conventional binder resins, various solvents, various additives, or the like to the dioxazine pigment of the present invention, in accordance with a preparation method of the related art. Specifically, it is possible to adjust a liquid ink by adjusting a base ink for a liquid ink having a high pigment concentration, and by using various binders, various solvents, various additives, or the like.

It is possible to produce the PU ink or the NC ink excellent in the initial viscosity and the storage stability, from the dioxazine pigment of the present invention, and the dioxazine pigment is preferable as an organic pigment composition for a gravure printing ink or a flexo printing ink. The PU ink contains a PU resin, a pigment, a solvent, and various additives, and the NC ink contains an NC resin, a pigment, a solvent, and various additives. The PU resin is not particularly limited insofar as a urethane structure is provided in the skeleton, and also includes polyurethane, polyurethane, polyurea, and the like. Examples of each of the solvents include an aromatic organic solvent such as toluene and xylene, a ketone-based solvent such as methyl ethyl ketone, methyl isobutyl ketone, cyclohexane, 2-heptanone, and 3-heptanone, an ester-based solvent such as ethyl acetate, n-propyl acetate, isopropyl acetate, isobutyl acetate, propylene glycol monoethyl ether acetate, and propylene glycol monomethyl ether acetate, an alcohol-based solvent such as methanol, ethanol, n-propanol, isopropanol, n-butanol, isobutanol, and t-butanol, a (poly)alkylene glycol monoalkyl ether-based solvent such as propylene glycol monoethyl ether, propylene glycol monomethyl ether, ethylene glycol monomethyl ether, ethylene glycol monoethyl ether, ethylene glycol mono-n-propyl ether, ethylene glycol mono-i-propyl ether, diethylene glycol monomethyl ether, diethylene glycol monoethyl ether, diethylene glycol mono-n-propyl ether, and diethylene glycol mono-i-propyl ether, a (poly)alkylene glycol monoalkyl ether acetate-based solvent such as ethylene glycol monomethyl ether acetate, ethylene glycol monoethyl ether acetate, diethylene glycol monomethyl ether acetate, and diethylene glycol monoethyl ether acetate, another ether-based solvent such as diethylene glycol dimethyl ether and diethylene glycol diethyl ether, and the like. Note that, the solvents may be independently used, or two or more types thereof may be used together. a surfactant such as an anionic surfactant, a nonionic surfactant, a cationic surfactant, and an amphoteric ionic surfactant, rosins such as gum rosin, polymerized rosin, disproportionation rosin, hydrogenated rosin, maleated rosin, cured rosin, and an alkyd phthalate resin, a pigment derivative, a dispersant, a wetting agent, an adhesion adjuvant, a leveling agent, an antifoaming agent, an antistatic agent, a trapping agent, an antiblocking agent, a wax component, and the like can be used as various additives.

In a case where the dioxazine pigment of the present invention is used as a printing ink, the printing ink using the dioxazine pigment of the present invention prepared as described above can be used by being diluted with ethyl acetate, a polyurethane-based varnish, or a polyamide-based varnish. In the preparation of the printing ink, a known conventional method can be adopted.

In a case where the dioxazine pigment of the present invention is a coating material as a colorant, as examples of a resin that is used as the coating material include various resins such as an acryl resin, a melamine resin, an epoxy resin, a polyester resin, a polyurethane resin, a polyamide resin, and a phenol resin.

Examples of a solvent that is used in the coating material include an aromatic-based solvent such as toluene, xylene, or methoxy benzene, an acetic acid ester-based solvent such as ethyl acetate, butyl acetate, propylene glycol monomethyl ether acetate, and propylene glycol monoethyl ether acetate, a propionate-based solvent such as ethoxy ethyl propionate, an alcohol-based solvent such as methanol, ethanol, propanol, n-butanol, and isobutanol, an ether-based solvent such as butyl cellosolve, propylene glycol monomethyl ether, diethylene glycol ethyl ether, and diethylene glycol dimethyl ether, a ketone-based solvent such as methyl ethyl ketone, methyl isobutyl ketone, and cyclohexane, an aliphatic hydrocarbon-based solvent such as hexane, a nitrogen compound-based solvent such as N,N-dimethyl formamide, γ-butyrolactam, N-methyl-2-pyrrolidone, aniline, and pyridine, a lactone-based solvent such as γ-butyrolactone, carbamate ester such as a mixture of methyl carbamate and ethyl carbamate of 48:52, water, and the like. In particular, a polar solvent that is water-soluble, such as a propionate-based solvent, an alcohol-based solvent, an ether-based solvent, a ketone-based solvent, a nitrogen compound-based solvent, a lactone-based solvent, and water, is suitable as the solvent.

In addition, in a case where a pigment additive and/or a pigment composition are dispersed and mixed in a liquid resin, and a resin composition for a coating material is obtained, general additives, for example, dispersants, fillers, coating material adjuvants, desiccants, plasticizers and/or adjuvant pigments can be used. This is attained by dispersing or mixing the components independently or collectively such that all of the components are collected, or by adding all of components at once.

Examples of a disperser for dispersing the composition containing the dioxazine pigment prepared in accordance with an application, as described above, include a known disperser such as a Disper, a homomixer, a paint conditioner, Scandex, a bead mill, Attritor, a ball mill, a two-roll mill, a three-roll mill, and a pressure kneader, but the disperser is not limited thereto. In the dispersion of the pigment composition, a resin and a solvent are added and dispersed such that a viscosity is obtained at which dispersion can be performed in the disperser. A coating material base having a high concentration after dispersion has a solid content of 5% to 20%, and is mixed with a resin and a solvent to be used as the coating material.

Hereinafter, the present invention will be described in more detail by using examples and comparative examples. In the following examples and comparative examples, unless otherwise noted, "%" indicates "mass %".

In this example, a dioxazine pigment having at least one hydroxy group and at least one carbonyl group on each surface of 23 particles of C.I. Pigment Violet was checked by a field desorption ionization mass spectrometry or a laser desorption ionization mass spectrometry. The details are as follows.

[Method According to Field Desorption Ionization Mass Spectrometry]

A mass spectrometric spectrum of the dioxazine pigment was measured by using JMS-T100GC manufactured by JEOL Ltd., in the field desorption ionization mass spectrometry. 5 mg of a sample was added to 1.0 mL of tetrahydrofuran not containing dibutyl hydroxy toluene (manufactured by Wako Pure Chemical Industries), was suspended with an ultrasound wave, and was used in the measurement.

[Measurement Condition]
Emitter Current: 0 mA to 40 mA [25.6 mA/minute]
Opposite Electrode: −10000 V
Measurement Mass Range: m/z=50 to 200
Measurement Time: 2 minutes In the mass spectrometric spectrum obtained by this condition, a molecular peak at 604 indicates C.I. Pigment Violet 23 having one hydroxy group, and a molecular peak at 618 indicates C.I. Pigment Violet 23 having two carbonyl groups.

[Method According to Laser Desorption Ionization Mass Spectrometry]

A mass spectrometric spectrum of the dioxazine pigment was measured by using JMS-S3000 manufactured by JEOL Ltd., in the laser desorption ionization mass spectrometry. 20 mg of a sample was added to 10 mL of ethanol (manufactured by Wako Pure Chemical Industries), was suspended with an ultrasound wave, and was used in a measurement solution. In addition, separately, 20 mg of sodium iodide (manufactured by Sigma-Aldrich Co. LLC.) was added to 10 mL of methanol (manufactured by Wako Pure Chemical Industries), was suspended with an ultrasound wave, and was used in a cationizing agent.

[Measurement Condition 1]

Measurement Sample: 1 µL of Measurement Solution is spotted on 384-spot measurement plate, manufactured by Hudson Surface Technology, Inc., and is dried in air.

Measurement Mode: Spiral TOF•Positive Mode
Laser Intensity: 45%
Delay Time: 120 nanosecond
Detector: 60%
Trace Count: 200 to 250 shots In the mass spectrometric spectrum obtained by this condition, a molecular peak at 604 indicates C.I. Pigment Violet 23 having one hydroxy group.

[Measurement Condition 2]

Measurement Sample: 1 µL of Measurement Solution and 1 µL of cationizing agent are spotted on 384-spot measurement plate, manufactured by Hudson Surface Technology, Inc., are mixed on the plate, and are dried in air.

Measurement Mode: Spiral TOF•Positive Mode
Laser Intensity: 45%
Delay Time: 120 nanosecond
Detector: 60%
Trace Count: 200 to 250 Shots In the mass spectrometric spectrum obtained by this condition, a molecular peak at 641 indicates molecules in which sodium ions of the cationizing agent are added to C.I. Pigment Violet 23 having two carbonyl groups.

In addition, in this example, a contact angle of the dioxazine pigment with respect to water and 1-bromonaphthalene was measured by an infiltration rate method. The details are as follows.

In the measurement, an automatic surface tensiometer Processor Tensiometer K12 (manufactured by KRUSS GmbH) was used. 1.5 g of a dioxazine pigment was filled in a measurement holder, a measurement liquid was infiltrated from the lower portion of the holder, and a wetting rate was measured as an option for measuring a powder wetting rate of the automatic surface tensiometer. First, a wetting rate of n-hexane was measured, an infiltration contact angle was assumed as 0°, and a filling constant was measured. Each dioxazine pigment was standardized on the basis of the measured filling constant such that a filling state thereof was the same. Subsequently, a wetting rate of each of water and 1-bromonaphthalene was measured, and the contact angle of the dioxazine pigment with respect to each of water and 1-bromonaphthalene was calculated by Washburn equation.

(Example 1) [Synthesis of Dioxazine Pigment (A-1)]

171.9 parts of a wet cake of C.I. Pigment Violet 23 (manufactured by DIC Corporation) (60 parts of a pigment) and 828.1 parts of ion exchange water were put into a stainless steel cup of 2 L, and were stirred with a Homodisper 2.5 Type (manufactured by PRIMIX Corporation) at the number of rotations of 500 rpm for 30 minutes. A slurry of C.I. Pigment Violet 23 was moved to a stainless steel cup of 5 L, and 2.75 parts of iron (II) sulfate heptahydrate (manufactured by Wako Pure Chemical Industries) was added and dissolved while performing stirring with a stainless steel anchor blade at the number of rotations of 150 rpm. Subsequently, 12.5 parts of 30% hydrogen peroxide water (manufactured by Wako Pure Chemical Industries) was added and was stirred for 30 minutes. Next, the slurry was subjected to Nutsche filtration, and was washed with 4 L of hot water of 70° C., and then, a filter product was subjected to blast drying (at 98° C. for 18 hours) by a blast isothermal drier WFO-500 (manufactured by TOKYO RIKAKIKAI CO., LTD.). A pigment lump that was obtained was pulverized, and thus, 58 parts of a dioxazine pigment (A-1) was obtained. The dioxazine pigment (A-1) was subjected to mass spectrometry by the laser desorption ionization mass spectrometry, and thus, the molecular peak at 604 was checked in the measurement condition 1, and the molecular peak at 641 was checked in the measurement condition 2. A contact angle of the dioxazine pigment (A-1) with water was 69.4°, and a contact angle of the dioxazine pigment (A-1) with respect to 1-bromonaphthalene was 67.7°.

(Example 2) [Synthesis of Dioxazine Pigment (A-2)]

58 parts of a dioxazine pigment (A-2) was obtained by the same operation as that of Example 1, except that the added amount of 30% hydrogen peroxide water was changed to 25 parts. The dioxazine pigment (A-2) was subjected to mass spectrometry by the laser desorption ionization mass spectrometry, and thus, the molecular peak at 604 was checked in the measurement condition 1, and the molecular peak at 641 was checked in the measurement condition 2. A contact angle of the dioxazine pigment (A-2) with respect to water was 57.2°, and a contact angle of the dioxazine pigment (A-2) with respect to 1-bromonaphthalene was 40.3°.

(Example 3) [Synthesis of Dioxazine Pigment (A-3)]

59 parts of a dioxazine pigment (A-3) was obtained by the same operation as that of Example 1, except that the added amount of 30% hydrogen peroxide water was changed to 50 parts. The dioxazine pigment (A-3) was subjected to field desorption ionization mass spectrometry, and thus, the molecular peaks at 604 and 618 were checked. Further, the dioxazine pigment (A-3) was subjected to mass spectrometry by the laser desorption ionization mass spectrometry, and thus, the molecular peak at 604 was checked in the measurement condition 1, and the molecular peak at 641 was checked in the measurement condition 2. A contact angle of the dioxazine pigment (A-3) with respect to water was 46.9°, and a contact angle of the dioxazine pigment (A-3) with respect to 1-bromonaphthalene was 45.3°.

(Example 4) [Synthesis of Dioxazine Pigment (A-4)]

58 parts of a dioxazine pigment (A-4) was obtained by the same operation as that of Example 1, except that the added amount of 30% hydrogen peroxide water was changed to 100 parts. The dioxazine pigment (A-4) was subjected to mass spectrometry by the laser desorption ionization mass spectrometry, and thus, the molecular peak at 604 was checked in the measurement condition 1, and the molecular peak at 641 was checked in the measurement condition 2. A contact angle of the dioxazine pigment (A-4) with respect to water was 58.4°, and a contact angle of the dioxazine pigment (A-4) with respect to 1-bromonaphthalene was 37.7°.

(Example 5) [Synthesis of Dioxazine Pigment (A-5)]

59 parts of a dioxazine pigment (A-5) was obtained by the same operation as that of Example 1, except that the added amount of iron (II) sulfate heptahydrate was changed to 11 parts, and the added amount of 30% hydrogen peroxide water was changed to 200 parts. The dioxazine pigment (A-5) was subjected to mass spectrometry by the field desorption ionization mass spectrometry, and thus, the molecular peaks at 604 and 618 were checked. Further, the dioxazine pigment (A-5) was subjected to mass spectrometry by the laser desorption ionization mass spectrometry, and thus, the molecular peak at 604 was checked in the measurement condition 1, and the molecular peak at 641 was checked in the measurement condition 2. A contact angle of the dioxazine pigment (A-5) with respect to water was 57.5°, and a contact angle of the dioxazine pigment (A-5) with respect to 1-bromonaphthalene was 32.9°.

(Example 6) [Synthesis of Dioxazine Pigment (A-6)]

515.8 parts of a wet cake of C.I. Pigment Violet 23 (manufactured by DIC Corporation) (180 parts of a pigment) and 2484.2 parts of ion exchange water were put into an enamel tank of 10 L, and were stirred with a Homodisper 2.5 Type (manufactured by PRIMIX Corporation) at the number of rotations of 500 rpm for 30 minutes. Next, a stirring blade was changed to a stainless steel anchor blade, and 8.25 parts of iron (II) sulfate heptahydrate (manufactured by Wako Pure Chemical Industries) was added and dissolved while performing stirring at the number of rotations of 100 rpm. Subsequently, a slurry was heated to 60° C. by using an electromagnetic heater, and then, 150 parts of 30% hydrogen peroxide water (manufactured by Wako Pure Chemical Industries) was dropped for 1 hour, and then, stirring was further performed for 15 minutes, the slurry was subjected to Nutsche filtration, and was washed with 12 L of hot water of 70° C., and then, a filter product was subjected to blast drying (at 98° C. for 18 hours) by a blast isothermal drier WFO-500 (manufactured by TOKYO RIKAKIKAI CO., LTD.). A pigment lump that was obtained was pulverized, and thus, 171 parts of a dioxazine pigment (A-6) was obtained. The dioxazine pigment (A-6) was subjected to mass spectrometry by the laser desorption ionization mass spectrometry, and thus, the molecular peak at 604 was checked in the measurement condition 1, and the molecular peak at 641 was checked in the measurement condition 2. A contact angle of the dioxazine pigment (A-6) with respect to water was 71.1°, and a contact angle of the dioxazine pigment (A-6) with respect to 1-bromonaphthalene was 49.4°.

(Comparative Example 1) [Synthesis of Dioxazine Pigment (A'-1)]

171.9 parts of a wet cake of C.I. Pigment Violet 23 (manufactured by DIC Corporation) (60 parts of a pigment) and 828.1 parts of ion exchange water were put into a stainless steel cup of 2 L, and were stirred with a Disper at the number of rotations of 500 rpm for 30 minutes. A slurry of C.I. Pigment Violet 23 was subjected to Nutsche filtration, and was washed with 4 L of hot water of 70° C., and then, a filter product was subjected to blast drying (at 98° C. for 18 hours) by a blast isothermal drier WFO-500 (manufactured by TOKYO RIKAKIKAI CO., LTD.). A pigment lump that was obtained was pulverized, and thus, 59 parts of a comparative dioxazine pigment (A'-1) was obtained. The dioxazine pigment (A'-1) was subjected to field desorption ionization mass spectrometry, but the molecular peaks at 604 and 618 were not observed. In addition, the dioxazine pigment (A'-1) was subjected to mass spectrometry by the laser desorption ionization mass spectrometry, but the molecular peaks at 604 and 641 were not observed in the measurement condition 1 and the measurement condition 2. A contact angle of the dioxazine pigment (A'-1) with respect to water was 90.0°, and a contact angle of the dioxazine pigment (A'-1) with respect to 1-bromonaphthalene was 85.6°.

(Comparative Example 2) [Synthesis of Dioxazine Pigment (A'-2)]

171.9 parts of a wet cake of C.I. Pigment Violet 23 (manufactured by DIC Corporation) (60 parts of a pigment) and 828.1 parts of ion exchange water were put into a glass beaker of 2 L, and were stirred with a Homodisper 2.5 Type (manufactured by PRIMIX Corporation) at the number of rotations of 500 rpm for 30 minutes. Next, a stirring blade was changed to a glass anchor blade, and the temperature was increased to 70° C. while performing stirring at the number of rotations of 150 rpm. 4 parts of a sulfonic acid derivative (manufactured by DIC Corporation) of C.I. Pigment Violet 23, dissolved in 100 parts of hot water of 70° C., was added to a slurry of C.I. Pigment Violet 23, and was stirred for 30 minutes. Subsequently, 6 parts of aluminum sulfate (manufactured by Wako Pure Chemical Industries), dissolved in 100 parts of hot water of 70° C., was added, and was stirred for 2 hours. The slurry was subjected to Nutsche filtration, and a filter product was subjected to blast drying (at 98° C. for 18 hours) by a blast isothermal drier WFO-500 (manufactured by TOKYO RIKAKIKAI CO., LTD.). A pigment lump that was obtained was pulverized, and thus, 59 parts of a dioxazine pigment (A'-2) was obtained. The dioxazine pigment (A'-2) was subjected to mass spectrometry by the laser desorption ionization mass spectrometry, but the molecular peaks at 604 and 641 were not observed in the measurement condition 1 and the measurement condition 2. A contact angle of the dioxazine pigment (A'-2) with respect to water was 89.9°, and a contact angle of the dioxazine pigment (A'-2) with respect to 1-bromonaphthalene was 48.5°.

[Preparation of Various Inks]

The evaluation of a polyurethane ink is as follows.

(Preparation of Polyurethane Ink)

In each of the dioxazine pigment obtained in Examples 1 to 6 and the comparative dioxazine pigment obtained in Comparative Examples 1 and 2, 5 parts of the dioxazine pigment, 25 parts of a polyurethane resin SANPRENE IB-501 (manufactured by Sanyo Chemical Industries, Ltd.), 13 parts of ethyl acetate (manufactured by Wako Pure Chemical Industries), 7 parts of isopropyl alcohol (manufactured by Wako Pure Chemical Industries), and 180 parts of ⅛-inch steel beads (manufactured by Mochiki Steel Ball Bearing Co., Ltd.) were put into polyethylene wide-mouth bottle of 250 mL, and were dispersed with a Paint Shaker (manufactured by Toyo Seiki Seisaku-sho, Ltd.) for 30 minutes. After that, 35 parts of a polyurethane resin SANPRENE IB-501 (manufactured by Sanyo Chemical Industries, Ltd.), 9.75 parts of ethyl acetate (manufactured by Wako Pure Chemical Industries), and 5.25 parts of isopropyl alcohol (manufactured by Wako Pure Chemical Industries) were additionally put into the wide-mouth bottle, and were dispersed with a Paint Shaker (manufactured by Toyo Seiki Seisaku-sho, Ltd.) for 5 minutes, and thus, each polyurethane ink was obtained.

(Measurement of Initial Viscosity of Polyurethane Ink)

The obtained polyurethane ink was left to stand in a thermostatic bath of 20° C. for 1 hour or longer, and an initial viscosity was measured by an R85 Type Viscosimeter RB85L (manufactured by TOKI SANGYO CO., LTD.) at a rotation rate of 30 rpm. It is excellent as the initial viscosity is low. In Table 1, evaluation was performed as follows.

Evaluation of Initial Viscosity of Polyurethane Ink (Viscosity at 30 rpm (Unit: mPa·s))

A: Less than 100
B: 100 or more and less than 1000
C: 1000 or more (Measurement of Viscosity of Polyurethane Ink after Stability Test)

The obtained polyurethane ink was left to stand in a multiplex safety type drier MSO-45TPH (manufactured by Futaba Chemical Co., Ltd.) at 50° C. for 7 days, and then, was left to stand in a thermostatic bath of 20° C. for 1 hour or longer, and a viscosity after a stability test was measured by an R85 Type Viscosimeter RB85L (manufactured by TOKI SANGYO CO., LTD.) at a rotation rate of 30 rpm. It is excellent as the viscosity after the stability test is low. In Table 1, evaluation was performed as follows.

Evaluation of Viscosity of Polyurethane Ink after Stability Test (Viscosity at 30 Rpm (Unit: mPa·s))

A: Less than 100
B: 100 or more and less than 1000
C: 1000 or more (Measurement of Gloss)

The obtained polyurethane ink was subjected to color spreading with respect to a PET film Lumirror 50T-60 (manufactured by PANAC INDUSTRIES, INC.) by a bar coater of No. 6, and the gloss of a color spreading film at 60° was measured with a glossimeter GM-268 Plus (manufactured by KONICA MINOLTA JAPAN, INC.). It is excellent as the gloss is large. In Table 1, evaluation was performed as follows.

Evaluation of Gloss of Color Spreading Film at 60°

A: 85 or more
B: 80 or more and less than 85
C: Less than 80

In each of the obtained polyurethane inks, the evaluation of the initial viscosity, the viscosity after the stability test, and the gloss of the color spreading film at 60° is shown in Table 1.

TABLE 1

| | Dioxazine pigment | Initial viscosity | Viscosity after stability test | Gloss at 60° |
|---|---|---|---|---|
| Example 1 | Dioxazine pigment (A-1) | B | B | B |
| Example 2 | Dioxazine pigment (A-2) | A | A | A |
| Example 3 | Dioxazine pigment (A-3) | A | A | A |
| Example 4 | Dioxazine pigment (A-4) | A | A | A |
| Example 5 | Dioxazine pigment (A-5) | A | A | A |
| Example 6 | Dioxazine pigment (A-6) | A | A | A |
| Comparative Example 1 | Dioxazine pigment (A'-1) | C | C | C |
| Comparative Example 2 | Dioxazine pigment (A'-2) | B | C | C |

As it is obvious from the comparison between Examples 1 to 6 and Comparative Examples 1 and 2, the polyurethane ink obtained by using the dioxazine pigment of the present invention has a lower initial viscosity and a lower viscosity after a stability test than those of the polyurethane ink obtained by the dioxazine pigment without any treatment or the dioxazine pigment treated with the sulfonic acid derivative of C.I. Pigment Violet 23. In addition, the polyurethane ink obtained by using the dioxazine pigment of the present invention has excellent performance that the gloss of the color spreading film at 60° is particularly high.

[Evaluation in NC Ink]

(Preparation of NC Varnish)

250 parts of an NC resin (Nitrogen: 10.7 to 12.2), 436.5 parts of ethanol (manufactured by Wako Pure Chemical Industries), and 13.5 parts of ethyl acetate (manufactured by Wako Pure Chemical Industries) were put into polyethylene wide-mouth bottle of 1 L, and were dispersed with a Paint Shaker (manufactured by Toyo Seiki Seisaku-sho, Ltd.) for 2 hours, and thus, an NC varnish was obtained.

(Preparation of NC Base Ink)

In each of the dioxazine pigment A-3 obtained in Example 3 and the dioxazine pigment A'-1 obtained in Comparative Example 1, 22 parts of the dioxazine pigment, 40 parts of the NC varnish, 36.9 parts of ethanol (manufactured by Wako Pure Chemical Industries), 1.1 parts of ethyl acetate (manufactured by Wako Pure Chemical Industries), and 150 parts of SAZ beads (manufactured by Tokyo Garasu Kikai Co., Ltd. ZirconiaYTZ Ball of 1.24) were put into a glass bottle of 200 mL, and were dispersed with Shaker Skandex SK550 (manufactured by Fast&Fluid Management B. V. Company) for 2 hours, and thus, an NC base ink was obtained.

(Preparation of Ink Diluted with Ethyl Acetate)

38.5 parts of the obtained NC base ink and 16.5 parts of ethyl acetate (manufactured by Wako Pure Chemical Industries) were put into a polyethylene wide-mouth bottle of 100 mL, and were dispersed with a Paint Shaker (manufactured by Toyo Seiki Seisaku-sho, Ltd.) for 10 seconds, and thus, an ink diluted with ethyl acetate was obtained.

(Measurement of Viscosity of NC Base Ink after Stability Test)

The obtained NC base ink was left to stand at a room temperature for 24 hours, and then, was left to stand in a thermostatic bath of 20° C. for 1 hour or longer, and a viscosity after a stability test was measured by R85 Type Viscosimeter RB85L (manufactured by TOKI SANGYO CO., LTD.) at 30 rpm. It is excellent as the viscosity after the stability test is low.

(Measurement of Viscosity of Ink Diluted with Ethyl Acetate)

The obtained ink diluted with ethyl acetate was left to stand in a thermostatic bath of 20° C. for 1 hour or longer, and a viscosity was measured by R85 Type Viscosimeter RB85L (manufactured by TOKI SANGYO CO., LTD.). It is excellent as the viscosity after being diluted with ethyl acetate is low.

Evaluation results in the NC ink are collectively shown in Table 2. A case where the dioxazine pigment (A-3) was used as the dioxazine pigment was set to Example 7, and a case where the dioxazine pigment (A'-1) was used as the dioxazine pigment was set to Comparative Example 3. Note that, the unit of various viscosities in Table 2 is mPa·s.

TABLE 2

|  | Dioxazine pigment | Viscosity after stability test | Viscosity after being diluted with ethyl acetate |
|---|---|---|---|
| Example 7 | Dioxazine pigment (A-3) | 3024 | 2240 |
| Comparative Example 3 | Dioxazine pigment (A'-1) | 3920 | 10800 |

As it is obvious from the comparison between Example 7 and Comparative Example 3, the NC ink obtained by using the dioxazine pigment of the present invention has a lower viscosity after a stability test and a lower viscosity after being diluted with ethyl acetate than those of the NC ink obtained by the dioxazine pigment without any treatment.

The invention claimed is:

1. A method for producing a dioxazine pigment, the method comprising:
    adding a dioxazine into a solvent with stirring to obtaining a pigment slurry; and
    adding an iron salt and hydrogen peroxide into the pigment slurry with stirring to obtain the dioxazine pigment,
    wherein the dioxazine is represented by formula (I):

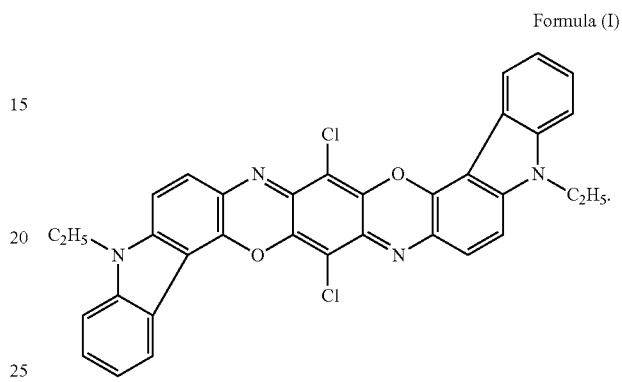

Formula (I)

2. The method for producing the dioxazine pigment according to claim 1, wherein the dioxazine pigment comprises particles having at least one hydroxy group and at least one carbonyl group on a surface thereof.

* * * * *